US012569667B2

(12) United States Patent
Palamarchuk et al.

(10) Patent No.: US 12,569,667 B2
(45) Date of Patent: Mar. 10, 2026

(54) CONTROL UNIT FOR OPERATING A BLOOD PUMP IN DIFFERENT CONVEYING MODES

(71) Applicant: Berlin Heart GmbH, Berlin (DE)

(72) Inventors: Evgenii Palamarchuk, Berlin (DE); Carsten Strauch, Berlin (DE)

(73) Assignee: Berlin Heart GmbH, Berlin (DE)

( * ) Notice: Subject to any disclaimer, the term of this patent is extended or adjusted under 35 U.S.C. 154(b) by 76 days.

(21) Appl. No.: 18/597,553

(22) Filed: Mar. 6, 2024

(65) Prior Publication Data

US 2024/0299731 A1 Sep. 12, 2024

(30) Foreign Application Priority Data

Mar. 7, 2023 (EP) ..................................... 23160611

(51) Int. Cl.
| | | |
|---|---|---|
| *A61M 60/242* | (2021.01) | |
| *A61M 60/546* | (2021.01) | |
| *A61M 60/806* | (2021.01) | |
| *F04D 15/00* | (2006.01) | |
| *F04D 29/22* | (2006.01) | |

(52) U.S. Cl.
CPC ........ *A61M 60/242* (2021.01); *A61M 60/546* (2021.01); *A61M 60/806* (2021.01); *F04D 15/00* (2013.01); *F04D 29/2283* (2013.01)

(58) Field of Classification Search
None
See application file for complete search history.

(56) References Cited

U.S. PATENT DOCUMENTS

| | | | | |
|---|---|---|---|---|
| 4,173,796 | A | * | 11/1979 | Jarvik ..................... F04D 15/00 |
| | | | | 417/389 |
| 4,863,344 | A | * | 9/1989 | Stefanini ............... F04D 29/247 |
| | | | | 415/141 |
| 9,011,312 | B2 | | 4/2015 | Bourque |
| 9,433,714 | B2 | | 9/2016 | Voskoboynikov et al. |
| 9,433,717 | B2 | | 9/2016 | Bourque |
| 2005/0085683 | A1 | | 4/2005 | Bolling et al. |
| 2022/0313889 | A1 | | 10/2022 | Simundic |

FOREIGN PATENT DOCUMENTS

| | | |
|---|---|---|
| CN | 108785771 A | 11/2018 |
| WO | WO 2012/040551 A1 | 3/2012 |
| WO | WO 2022/036070 A1 | 2/2022 |

OTHER PUBLICATIONS

European Search Report for EP Application No. 23160611.2 dated Aug. 30, 2023 (German language only) (8 pp.).

* cited by examiner

*Primary Examiner* — Kenneth J Hansen
(74) *Attorney, Agent, or Firm* — Crowell & Moring LLP

(57) ABSTRACT

A blood pump with a rotor can be driven to rotate about an axis of rotation for conveying blood. A control is being configured to operate the rotor successively in time, or alternately several times, in a first conveying mode and at least in one second conveying mode. In order to avoid dead water areas in the region of the rotor and possible thrombus formation the direction of rotation of the rotor is reversed in the second conveying mode compared to operation in the first conveying mode.

18 Claims, 3 Drawing Sheets

CONTROL UNIT FOR OPERATING A BLOOD PUMP IN DIFFERENT CONVEYING MODES

PRIORITY

This application claims priority to EP Application No. 23 160 611.2, filed on Mar. 7, 2023, the entirety of which is hereby fully incorporated by reference herein.

TECHNICAL FIELD

The application relates to medical technology and mechanical engineering as well as fluid mechanics and can be used in the field of blood pumps.

BACKGROUND

Blood pumps to support or replace a patient's heart function have been used successfully for some time. Various forms of pumps are known, some of which are implantable and others are stationary or worn on the patient's body. In many cases, it is reasonable to implant blood pumps if possible. VAD (ventricular assist device) pumps are a special group of implantable pumps. These can be implanted in such a way that they are connected to a cardiac ventricle and draw blood from there, which is then fed into the patient's vascular system.

In some cases, such VAD pumps are formed as rotary pumps and therefore have a drivable rotor for conveying blood. Some pumps may take measures to avoid or minimize so-called dead water areas with poor flow within the pump or in its immediate vicinity. Such dead water areas can possibly lead or contribute to thrombus formation.

Implantable VAD rotary pumps may have the speed of the pump is varied in order to enable pulsatile operation of such a pump, which imitates or supports the natural mode of operation of a functioning heart, and then again to counteract thrombus formation. In this context, the patent specifications U.S. Pat. Nos. 9,433,714 B2, 9,433,717 B2, 9,011,312 and EP 2 618 863 B1 have become known, for example. These documents each disclose methods in which a speed control reduces and/or increases the speed of a blood pump within certain limits and according to certain time patterns.

SUMMARY

The present embodiments are based on the task of creating a system with a blood pump that further reduces the manifestation, frequency and/or probability of the formation of dead water areas.

The task may be solved with the features of the embodiments according to patent claim 1 by a system with a blood pump and a control unit. In addition, the embodiments relate to a machine-readable storage medium with instructions for a control unit, which enable a blood pump to be operated in accordance with the embodiments, and to a method for operating a blood pump with a rotor that can be driven.

The embodiments relate to a system comprising a blood pump with a rotor which can be driven to rotate about an axis of rotation for conveying blood and a control unit for a blood pump, the control unit being configured to operate the rotor successively in time, in particular alternately several times, in a first conveying mode A and at least in one second conveying mode B.

The task may be solved according to the embodiments by reversing the direction of rotation of the rotor in the second conveying mode compared to operation in the first conveying mode. By reversing the direction of rotation of the rotor compared to operation in the first conveying mode, the direction of inflow to the rotor is reversed and thus qualitatively changed in a step change compared to a mere change in speed. This means that other areas of the rotor can be more exposed to the blood flow than is possible with a gradual change in speed while the direction of rotation remains the same. This reduces the formation of dead water areas in areas of the rotor that cannot be achieved by changing the speed only in terms of amount. Compared to the state of the art, the embodiments ensure that areas within the rotor are at least temporarily well flowed through and thus kept free from the formation of dead water areas in which, according to the state of the art, risks of thrombus formation can occur.

One embodiment can provide, that the rotor is configured in such a way that the conveying direction of the blood pump in the second conveying mode B is the same as in the first conveying mode A.

Since the conveyance of the blood in radial or diagonal (mixed radial/axial) conveying rotary pumps is usually ensured by a centrifugal force within the rotor, the conveying direction of the blood in the pump remains unchanged in such pumps regardless of the direction of rotation of the rotor. The efficiency of the pump can change depending on the direction of rotation, but the blood is prevented from flowing back when the direction of rotation is changed. It therefore is reasonable in many cases for the rotor to be configured to convey a liquid, in particular blood, in a radial or diagonal direction. In some cases, however, the embodiments can also be used to advantage with axially pumping rotary pumps.

It may also be provided that the rotor has one or more conveying elements, in particular in the form of blades.

Such conveying elements can, for example, be attached to a hub and project radially outwards from it or, in another embodiment, conveying elements can also be arranged on a disk-shaped carrier with a central flow opening. The conveying elements usually have conveying surfaces that are arranged on a pressure side of the respective conveying element, wherein however in a reverse speed operation/second conveying mode there are also conveying surfaces on the opposite side of the conveying elements that are arranged on the suction side of the rotor in normal operation/first conveying mode. Conveying elements and, if necessary, conveying surfaces can be straight/flat or curved in one or more directions, wherein the conveying surfaces extend at least partially in the radial direction of the rotor.

Thus one embodiment can provide that at least one, in particular two or more than two blades of the rotor or the conveying surfaces located on the pressure side of the respective blades in the first conveying mode extend, respectively, as viewed in the direction parallel to the axis of rotation, from a first point, which has a first distance to the axis of rotation, in a straight or curved course to a second point, which has a second, greater distance to the axis of rotation than the first point.

Viewed in the direction of the axis of rotation of the rotor, one or more of the conveying elements can, for example, have the shape of a section of a spiral and be arranged symmetrically around a flow opening that is formed centrally within a carrier of the blades. The blood to be conveyed then flows in through the flow opening and is conveyed outwards by centrifugal forces as part of the rotational movement of the rotor. The individual conveying elements then have inflow edges or inflow areas that are arranged at the radially inner end of each conveying element. The conveying elements of a rotary pump are usually designed in such a way that the pump has a significantly higher efficiency in a first direction of rotation than in a second direction of rotation of the rotor. The radially inner inflow edges of the conveying elements are subjected to different inflows by the liquid to be conveyed within certain limits depending on the speed. By reversing the direction of rotation, completely new areas and possibly also different sides of a conveying element are actually additionally exposed to a flow, so that with a changing direction of rotation, the entire area in the vicinity of the radially inner inflow area of each conveying element is exposed to an increased flow at certain times and thus a permanent formation of dead water areas can be prevented to a greater extent.

The rotor of an implantable blood pump is often designed asymmetrically in such a way that when operating in a first direction of rotation of the rotor, which is used in a first conveying mode, for example, a significantly higher conveying efficiency is achieved than when operating in the opposite direction of rotation, which can be used in a second conveying mode. Here, it can be provided, for example, that the blades of the rotor or the conveying surfaces located on the pressure side of the respective blades in the first conveying mode each extend, as viewed in the direction parallel to the axis of rotation, radially outwards from the axis of rotation and in particular have a tangential component with respect to the rotor at least in sections in their course.

The operation of such a blood pump will then be designed in such a way that it is predominantly operated in the first conveying mode with a direction of rotation that corresponds to the optimized efficiency of the pump. Time periods in which the pump is operated in the opposite direction of rotation of the rotor will be shorter in duration and may involve shorter time intervals on a regular or irregular basis.

The time periods in which the pump is operated in the first conveying mode can, for example, comprise more than 80%, in particular more than 90%, further in particular more than 95%, further in particular more than 99% of the operating time, while the time periods of operation in the second conveying mode can comprise less than 20%, in particular less than 10%, further in particular less than 5% and further in particular than 1% of the operating time. Individual time intervals in which the blood pump is operated in the second conveying mode can, for example, be shorter than one second, in particular shorter than 0.5 seconds, and further in particular shorter than 0.2 or shorter than 0.1 second. The frequency with which time sections of the second conveying mode are activated during operation can, for example, be designed so that a time section of the second conveying mode takes place at least every two seconds, in particular at least every 1.5 seconds. A regular time interval between two time periods of the second conveying mode can therefore be less than 5 seconds, in particular less than 3 seconds. In another embodiment, however, it is also possible that the time periods of the second conveying mode are activated less frequently and, for example, occur less frequently than once per minute, in particular also less frequently than once every 10 minutes or less frequently than 1 time per hour.

Typical speeds in the first conveying mode can be between 2000 rpm and 5300 rpm, for example, while speeds in the second conveying mode can be between 1000 rpm and 2500 rpm or up to 4000 rpm, for example. The speeds in reverse mode/second operating mode, for example, can also be less than 500 rpm or even less than 200 rpm.

The frequency with which it is necessary to activate time periods of the second conveying mode depends on the geometric design of the rotor or the conveying elements. In a special configuration of the operation, it may also be provided that the speed is increased in the first conveying mode shortly before the second conveying mode is activated and then reduced to zero and brought to negative speeds, i.e. to a speed reversal mode. After completion of the second conveying mode, which can last 0.1 or 0.5 seconds or less than 1 second, for example, the speed is then reversed again and increased to a constant speed of the first conveying mode.

The embodiments relate, in addition to a system of the above described kind, also to a control unit for a blood pump with a rotor which can be driven to rotate about an axis of rotation for conveying blood that is configured to operate the rotor successively in time in a first conveying mode and at least in a second conveying mode, wherein in the second conveying mode the direction of rotation of the rotor is reversed with respect to operation in the first conveying mode.

In addition, the embodiments relate to a machine-readable storage medium which is coded with instructions which, when executed by a control unit implemented as a data processing device, cause the control unit to operate the rotor successively in time in a first conveying mode and at least in one second conveying mode, wherein in the second conveying mode the direction of rotation of the rotor is reversed with respect to operation in the first conveying mode.

Further the embodiments relate to a method for operating a blood pump with a rotor which can be driven to rotate about an axis of rotation for conveying blood, where the rotor is operated successively in time in a first conveying mode and at least in one second conveying mode, wherein in the second conveying mode the direction of rotation of the rotor is reversed with respect to the operation in the first conveying mode.

A particular configuration of the method can be provided in that the rotor is regularly operated alternately in the first and second conveying modes A, B, wherein in particular the proportion of time of operation in the first conveying mode is greater than the proportion of time of operation in the second conveying mode, in particular at least 5 times greater or at least 10 times greater or at least 100 times greater.

The embodiments are shown and explained in detail below with reference to embodiments in figures of a drawing.

BRIEF DESCRIPTION OF THE DRAWINGS

Herein are shown in

DETAILED DESCRIPTION

Figures 1, 2:
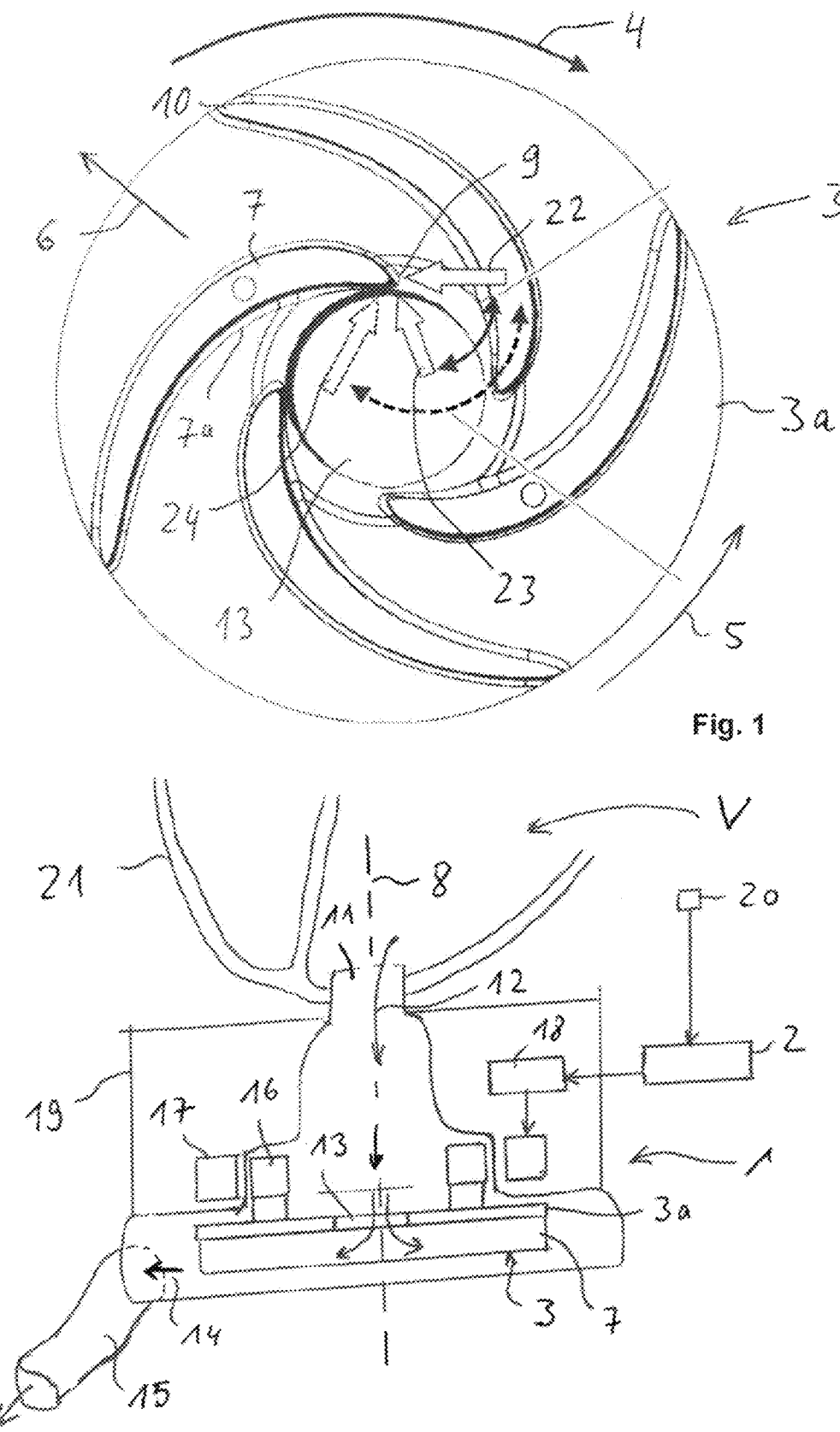
FIG. 1 shows a rotor of a blood pump in a schematic front view.
FIG. 2 shows a cross-sectional view of a blood pump implanted in a patient's body.

FIG. 1 shows the rotor 3 of an implantable VAD blood pump with four conveying elements in the form of blades, of which the conveying element 7 is shown in more detail as an example. The viewing direction of FIG. 1 is parallel or along the axis of rotation 8, which can be seen in FIG. 2 and is perpendicular to the drawing plane in FIG. 1. In the example shown, the rotor 3 has a disk-shaped carrier 3a, which can also be seen in FIG. 2 and on which several conveying elements are arranged symmetrically. In a first conveying mode A, in which the blood pump is optimized and operated with the best possible efficiency, the direction of rotation is indicated by arrow 4 in FIG. 1. As can be seen in FIG. 2, the blood flows in from a ventricle V of a heart through a suction opening 11 of the blood pump 1 in the direction of the arrow 12. Furthermore, the blood flows through the flow opening 13 of the rotor 3 and is conveyed from there in the radial direction 6 of the rotor by the rotation of the rotor and the conveying elements and the associated centrifugal acceleration. In FIG. 2, the arrow 14 indicates the outflow direction of the blood to a pump outlet 15.

The rotor 3 is moved by means of an armature 16, which in turn is driven by a stator 17 arranged outside the fluid channel. The blood pump 1 together with the drive control 18 is arranged in a schematically illustrated pump housing 19, wherein the pump housing 19 is designed in such a way that it can be implanted in the body of a patient in a way that is compatible with the body. An arrangement of the drive on the inlet side of the pump, as seen from the rotor, is shown, wherein, however, an arrangement on the outlet side of the pump, as seen from the rotor, is also conceivable.

The blood pump is controlled by a control unit 2, which can be located either inside the pump housing 19, outside the pump housing in the patient's body or outside the body.

The control unit 2 can also be connected to a sensor 20 that detects the contraction movement of the patient's heart 21 so that the operation of the blood pump 1 can be synchronized with the contraction movement of the heart 21. Here, it is possible to reverse the movement of the rotor during systole, but it is also possible to reverse the movement during diastole, which results in greater flushing of the pump.

FIG. 1 shows in detail how the blood flowing into the pump flows against the inflow edge or the inflow area of the conveying element 7 in the area of point 9 radially inwards in relation to the rotor 3. Depending on the rotational speed of the rotor, when the rotor rotates in the direction shown by arrow 4, i.e. in the first conveying mode A, the main direction of flow of the blood relative to the conveying element 7 is set between arrows 22 and 23. A certain region of the conveying element 7 on its side 7a, which forms the suction side of the blade 7 in the first conveying mode, is not reached during operation in the direction of rotation 4, even if the speed varies. If, on the other hand, the direction of rotation is reversed at negative speeds, as indicated by the arrow 5, the inflow is directed towards a significantly larger region on the side 7a of the conveying element 7, which forms the pressure side in this operation. The extended inflow area is indicated by arrow 24. If the entire spectrum of two opposite directions of rotation of the rotor is used, the angular range between arrows 22 and 24 can be utilized and the inflow can be directed at the conveying element 7 from all directions between arrows 22 and 24. This results in considerably improved possibilities for avoiding dead water areas on the rotor.

It can be seen that in both directions of rotation 4, 5 of the rotor 3, the conveying direction of the rotor is maintained radially from the inside to the outside, as shown by the arrow 6. However, the efficiency and performance of the pump is different in conveying modes A and B with the design of the conveying elements 7 shown. The direction of rotation 4 of the rotor 3 corresponds to the first conveying mode A and therefore the operation that is predominantly set, while the direction of rotation 5 corresponds to the second conveying mode B and therefore the less efficient conveying mode.

Figure 3:
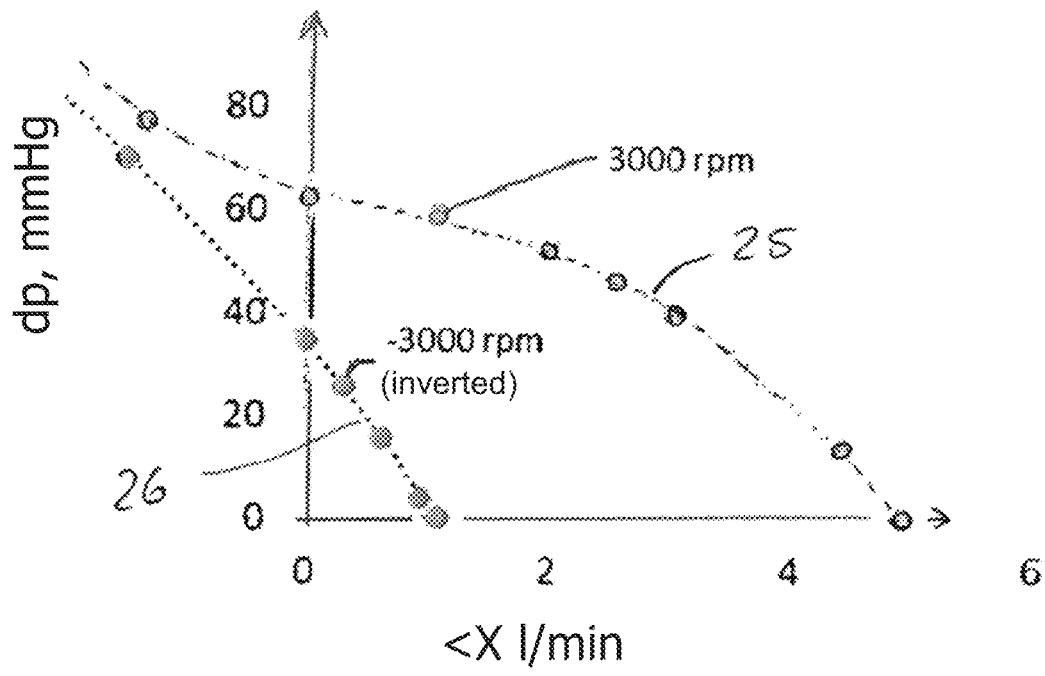
FIG. 3 shows two characteristic curves of a blood pump for operation in a first and a second conveying mode.

FIG. 3 shows characteristic curves of the pumps shown for the two different directions of rotation 3 and 4, wherein the upper line 25 corresponds to the direction of rotation 4 from FIG. 3 and the first conveying mode A, while the lower line 26 corresponds to the direction of rotation 5 and the second conveying mode B. In FIG. 3, the conveying rate of the pump is plotted on the horizontal axis and the generated pressure on the vertical axis. The work point at a rotation speed of 3000 rpm is marked in both lines and it can be seen that the pressure generation and also the conveying rate are significantly reduced in the case of curve 26 compared to curve 25.

Figure 4:
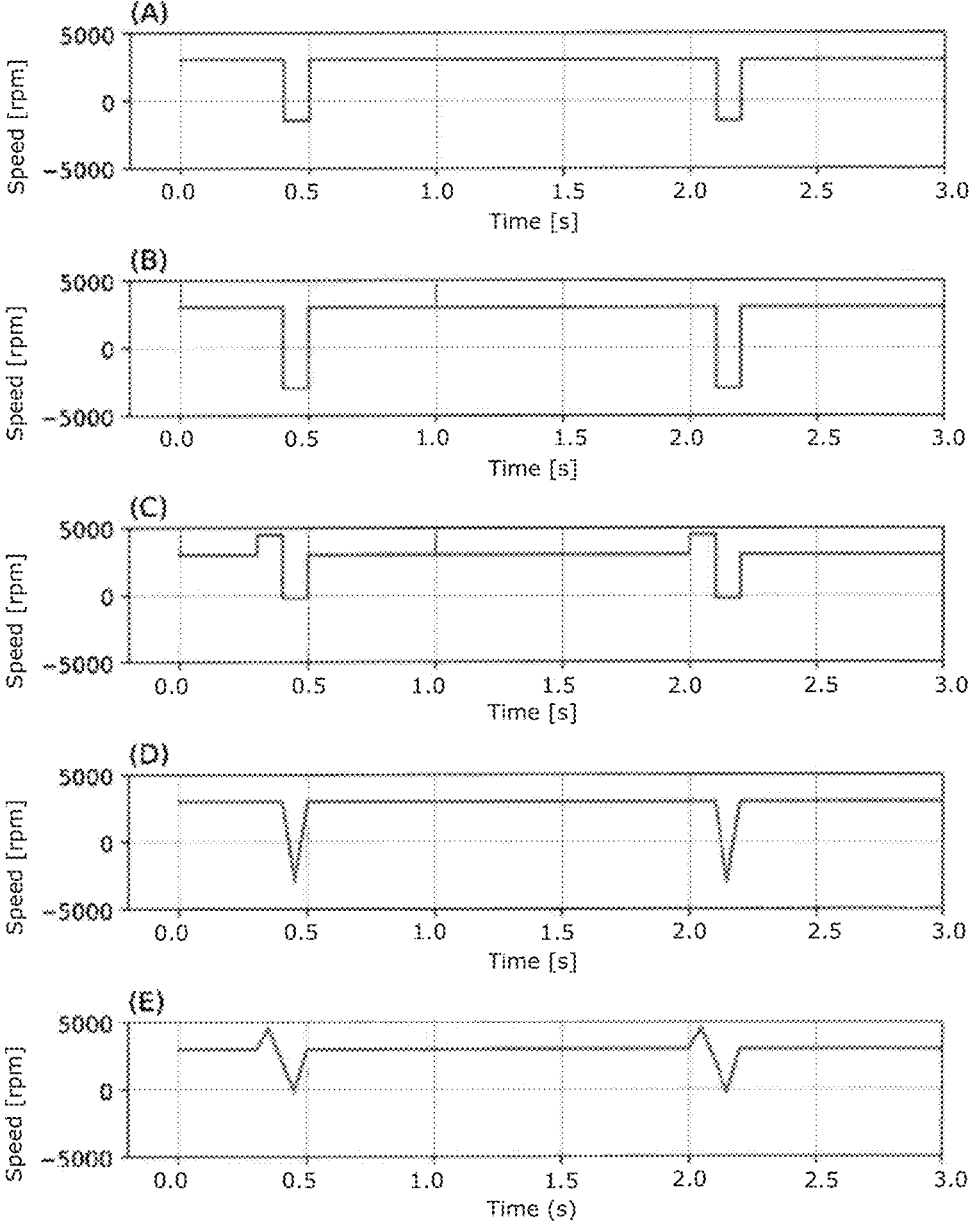
FIG. 4 shows five time-diagrams, each representing a speed sequence of a blood pump over a period of time.

FIG. 4 shows five diagrams, one above the other, in each of which the course of the rotor speed is shown over a period of time of 2.5 to 3 seconds. In the case of the top diagram, the upper line corresponds to the first conveying mode A, wherein a speed of slightly more than 2500 rpm is set for most of the time. After about 0.4 seconds, the speed is reduced and reversed to around 2000 rpm in the opposite direction of rotation. After a further 0.1 seconds or so, the speed is reversed again and the pump continues to operate in the first conveying mode A. This pattern is repeated approximately every 1.5 seconds.

The second diagram shows that initially the pump is operated in the first conveying mode A at slightly more than 2500 rpm, that after about 0.4 seconds the speed is reduced and brought to about 3000 rpm in the opposite direction and is thereby reversed. The pump is then in the second conveying mode B for approximately 0.4 seconds to 0.5 seconds and is then decelerated and operated in the opposite direction, so that a transition to conveying mode A takes place again, which predominantly characterizes the operation of the pump in terms of time. This pattern is also repeated approximately every 1.5 seconds.

The third diagram shows a scheme in which the pump is initially operated in the first delivery mode A at a speed of about 3000 rpm, then increases the speed to about 4000 rpm shortly before the direction of rotation is reversed and maintains this increased speed for about a tenth of a second in the manner of a pulse. The speed is then reduced and reversed, wherein the reversed speed remains limited to a few revolutions per minute, for example less than 500 rpm or less than 300 rpm. This conveying mode B with reversed direction of rotation is also maintained for approximately one tenth of a second and at a time of 0.5 seconds there is a transition to conveying mode A, which is maintained for most of the time. This pattern is also repeated approximately every 1.5 seconds.

It should be noted that the repetition frequency can also be higher than once every 1.5 seconds. On the other hand, the reversal of the direction of rotation can also take place much less frequently, for example, there can also be at least half a minute or at least one minute or even an interval of at least several minutes or at least one hour between the time intervals in which the direction of rotation is reversed. This essentially depends on the design of the pump rotor and the tendency to thrombus formation.

The fourth diagram shows that, starting from operation in the first conveying mode at a speed of around 3000 rpm, the speed is decelerated to zero via a steep ramp and accelerated to negative speeds/in the reverse direction up to an absolute speed of at least 1000 rpm, in the example shown up to around 3500 rpm, in order to be decelerated again immediately on reaching a maximum speed in the reverse direction and accelerated to the initial speed in the first conveying mode via a further ramp. In the second conveying mode B with reversed direction of rotation, no time interval with constant speed is therefore provided.

A structurally similar course as in the fourth diagram is also shown in the fifth diagram, wherein in the first conveying mode, a short pulse-like increase in speed takes place first before braking and the rotor is then brought to negative speeds via a ramp while reversing the direction of rotation. In the reverse direction of rotation, the speed is limited to a few 100 rpm, for example 500 rpm or 300 rpm. In this example, the highest speed in the reverse direction is also only reached at certain points, without a constant speed being achieved over a time interval. This means that no stationary flow conditions can develop during the rotation reversal, which further counteracts the formation of dead water areas.

The described system and the method for controlling the pump rotor of a blood pump can prevent or significantly reduce thrombus formation. As shown above, by reversing the direction of rotation, dead water areas at the rotor can be avoided in regions that cannot be reached if the direction of rotation of the pump remains the same.

The invention claimed is:

1. A system comprising:
   a blood pump with a rotor which can be driven to rotate about an axis of rotation for conveying blood; and
   a control unit for the blood pump that is configured to operate the rotor in a first conveying mode and at least in one second conveying mode, wherein the second conveying mode comprises a direction of rotation of the rotor is reversed with respect to a direction of rotation of the rotor in the first conveying mode;
   wherein the rotor is configured such that a conveying direction of the blood pump in the second conveying mode is the same as a conveying direction of the blood pump in the first conveying mode.

2. The system according to claim 1, wherein the rotor is configured to convey a liquid in a radial direction, in an axial direction, or in a diagonal direction.

3. The system according to claim 2, wherein the liquid comprises blood.

4. The system according to claim 1, wherein the rotor comprises one or more conveying elements.

5. The system according to claim 4, wherein the one or more conveying elements comprise blades.

6. The system according to claim 5, wherein at least two blades of the rotor extend, as viewed in the direction parallel to the axis of rotation, from a first point to a second point in a straight or curved course.

7. The system according to claim 6, wherein the first point has a first distance to the axis of rotation and the second point has a second distance that is a greater distance to the axis of rotation than the first point.

8. The system according to claim 7, wherein the blades of the rotor each extend, as viewed in the direction parallel to the axis of rotation, radially outwards from the axis of rotation and have a tangential component with respect to the rotor.

9. The system according to claim 1, wherein the control unit is configured to operate the rotor successively in time in the first conveying mode and in the second conveying mode.

10. The system according to claim 1, wherein the control unit is configured to operate the rotor alternately several times in the first conveying mode and in the second conveying mode.

11. A method for operating a blood pump with a rotor, the method comprising:
   driving the rotor to rotate about an axis of rotation for conveying blood;
   operating the rotor in a first conveying mode; and
   operating the rotor in at least one second conveying mode, wherein a direction of operation of the rotor for the at least one second conveying mode is reversed with respect to a direction of operation of the rotor for the first conveying mode;
   wherein the conveying direction of the blood pump in the second conveying mode is the same as a conveying direction of the blood pump in the first conveying mode.

12. The method according to claim 11, wherein the rotor is regularly operated alternately in the first conveying mode and the second conveying mode.

13. The method according to claim 12, wherein a proportion of time of operation in the first conveying mode is greater than the proportion of time of operation in the second conveying mode.

14. The method according to claim 13, wherein the proportion of time of operation of the first conveying mode at least 10 times greater than the second conveying mode.

15. The method according to claim 11, further comprising:
   conveying blood in a radial direction, in an axial direction, or in a diagonal direction.

16. The method according to claim 11, wherein the rotor includes one or more blades.

17. The method according to claim 16, wherein at least two blades of the rotor are disposed on a pressure side of the respective blades in the first conveying mode and extend, as viewed in the direction parallel to the axis of rotation, from a first point to a second point in a straight or curved course.

18. The method of claim 17, wherein the first point has a first distance to the axis of rotation and the second point has a second distance that is a greater distance to the axis of rotation than the first point.

* * * * *